United States Patent [19]

Billington et al.

[11] Patent Number: 5,422,365
[45] Date of Patent: Jun. 6, 1995

[54] NAPHTHALENE COMPOUNDS

[75] Inventors: David Billington, Levallois Perret; Francoise Perron-Sierra; Isabelle Picard, both of Paris; Jacques Duhault, Croissy sur Seine; Joseph Espinal, Paris, all of France

[73] Assignee: Adir et Compagnie, Courbevoie, France

[21] Appl. No.: 289,763

[22] Filed: Aug. 12, 1994

[30] Foreign Application Priority Data

Aug. 18, 1993 [FR] France ................. 93 10069

[51] Int. Cl.⁶ ............... A61K 31/34; A61K 31/335; C07D 303/06; C17C 35/36
[52] U.S. Cl. .................. 514/468; 514/475; 514/546; 514/548; 514/715; 514/729; 549/457; 549/459; 549/545; 549/546; 560/256; 568/665; 568/817; 568/819
[58] Field of Search ............ 568/665, 817, 819; 549/457, 459, 545, 546; 514/468, 475, 546, 548, 715, 729; 560/256

[56] References Cited

U.S. PATENT DOCUMENTS

| | | | |
|---|---|---|---|
| 2,912,462 | 11/1959 | Goldstein et al. | 568/819 |
| 4,138,497 | 2/1979 | Hauck et al. | 514/548 |
| 4,346,227 | 8/1982 | Terahara et al. | 560/256 |
| 4,820,865 | 4/1989 | Terahara et al. | 560/256 |
| 5,173,487 | 12/1992 | Saunders et al. | 514/548 |
| 5,177,104 | 1/1993 | Varma et al. | 514/548 |
| 5,276,055 | 1/1994 | Cabello et al. | 560/256 |

*Primary Examiner*—Joseph E. Evans
*Attorney, Agent, or Firm*—Gordon W. Hueschen

[57] ABSTRACT

A compound selected from those of formula (I):

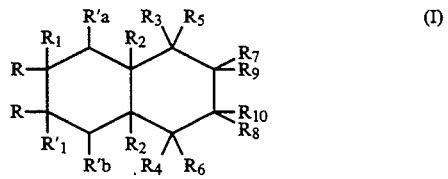

wherein:
$R_1$, $R'_1$ and $R_2$ are each selected, independently of the others, from hydrogen and an alkyl radical, the two $R_2$ groups being in the cis position in relation to the rings, and R, $R_3$, $R_4$, $R_5$, $R_6$, $R_7$, $R_8$, $R_9$, $R_{10}$, $R'a$ and $R'b$ are as defined in the description, useful therapeutically in the regulation of the secretion of insulin.

11 Claims, No Drawings

NAPHTHALENE COMPOUNDS

The present invention relates to new naphthalene compounds that are partially or fully hydrogenated and substituted by at least two hydroxy, alkoxy or acyloxy groups, to a process for their preparation and to pharmaceutical compositions containing them.

The applicant has discovered that those new naphthalene compounds exhibit remarkable pharmacological properties. In particular they prove to be powerful regulators of insulin secretion and as such may be used in the treatment of diabetes, insulin resistance, cardiovascular disorders and insulinomas.

The present invention relates more especially to compounds of formula (I):

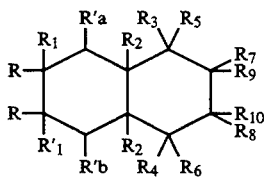

(I)

wherein:
R represents a radical selected from hydroxy, alkoxy and acyloxy,
$R_1$, $R'_1$ and $R_2$ are each selected, independently of the others, from hydrogen and alkyl, the two $R_2$ groups being in the cis position in relation to the rings,
$R_3$ and $R_4$ each represents hydrogen or together form a methylene or ethylene bridge,
$R_5$ and $R_6$ are each selected, independently of the other, from hydrogen, hydroxy, alkoxy, acyloxy and alkyl,
$R_7$ and $R_8$ are each selected, independently of the other, from hydrogen and alkyl,
$R_9$, $R_{10}$, $R'a$ and $R'b$
are each selected, independently of the others, from hydrogen, hydroxy, alkoxy and acyloxy,
or $R_9$ and $R10$ together form a double bond or a ring with an oxygen atom and $R'a$ and $R'b$ are as defined above,
or $R_9$ and $R'a$ together form a ring with an oxygen atom and $R_{10}$ and $R'b$ are as defined above,
or $R_{10}$ and $R'b$ together form a ring with an oxygen atom and $R_9$ and $R'a$ are as defined above,
it being understood that the terms "alkyl", "alkoxy" and "acyloxy" denote straight-chain or branched groups having 1 to 6 carbon atoms inclusive, their stereoisomers, and also their possible pharmaceutically-acceptable addition salts with a base.

The present invention relates also to a process for the preparation of compounds of formula
(I) which is characterised in that a quinone of formula (II) and a diene of formula (III):

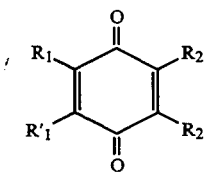

(II)

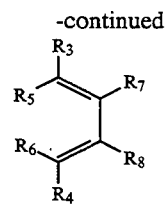

(III)

wherein $R_1$, $R'_1$, $R_2$, $R_3$, $R_4$, $R_5$, $R_6$, $R_7$ and $R_8$ are as defined above,
are subjected to a Dieis-Alder reaction in a non-polar solvent, such as toluene, with the application of heat, for example at a temperature of from 40° to 80° C., under an inert atmosphere, to obtain the intermediate of formula (IV):

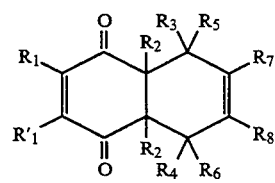

(IV)

wherein $R_1$, $R'_1$, $R_2$, $R_3$, $R_4$, $R_5$, $R_6$, $R_7$ and $R_8$ are as defined above,
which, after separation of the possible stereoisomers in accordance with a conventional method of separation, is then subjected to the action of a reducing agent, for example lithium aluminium hydride or sodium borohydride, in the presence of cerium chloride, in an anhydrous solvent, such as methanol, dichloromethane, dimethylformamide or tetrahydrofuran, at an appropriate temperature, that is from 0° to 22° C., to obtain the diol of formula ($V_a$):

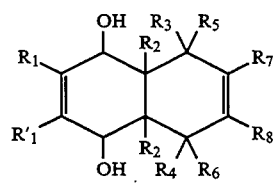

($V_a$)

wherein $R_1$, $R'_1$, $R_2$, $R_3$, $R_4$, $R_5$, $R_6$, $R_7$ and $R_8$ are as defined above,
which, after separation of the possible stereoisomers in accordance with a conventional method of separation, may be subjected to the action of an oxidising agent, such as 3-chloroperbenzoic acid, to yield the compounds of formulae ($V_{a1}$) and ($V_{a2}$), separated in accordance with a conventional method of separation:

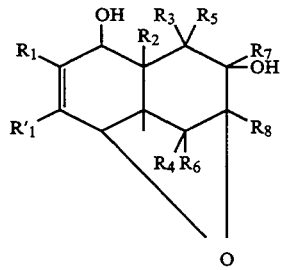

($V_{a1}$)

-continued

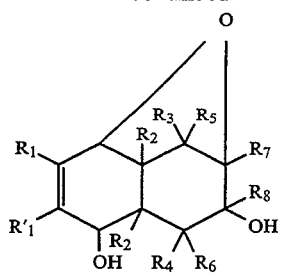
(V$_{a2}$)

wherein R$_1$, R'$_1$, R$_2$, R$_3$, R$_4$, R$_5$, R$_6$, R$_7$ and R$_8$ are as defined above, the hydroxy functions of which compounds of formulae (V$_a$), (V$_{a1}$) and (V$_{a2}$) may be alkylated or acylated in accordance with conventional methods of alkylation or acylation, respectively, the compounds of formulae (V$_a$), (V$_{a1}$) and (V$_{a2}$) and their optional alkylation and acylation products then being hydroxylated

- in the case of cis-hydroxylation by conventional methods, such as osmylation (osmium tetroxide in the presence of a co-oxidant), or oxidation by potassium permanganate, in polar solvents, such as tert-butanol, tetrahydrofuran, acetone, water or pyridine,
- in the case of trans-hydroxylation by epoxidation, for example using 3-chloroperbenzoic acid, followed by treatment in acidic medium, for example trifluoroacetic acid or acetic acid, to yield, respectively, after separation of the possible stereoisomers in accordance with conventional methods of separation, compounds of formulae (VI$_a$), (VI$_{a1}$) and (VI$_{a2}$):

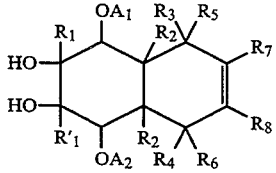
(VI$_a$)

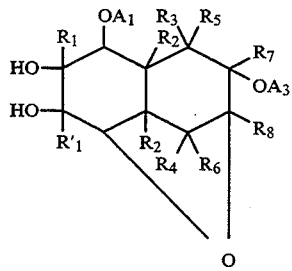
(VI$_{a1}$)

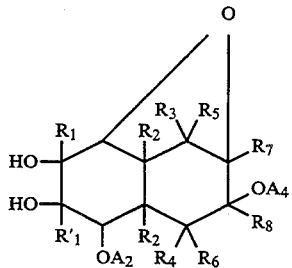
(VI$_{a2}$)

wherein R$_1$, R'$_1$, R$_2$, R$_3$, R$_4$, R$_5$, R$_6$, R$_7$ and R$_8$ are as defined above and A$_1$, A$_2$, A$_3$ and A$_4$ each represents, independently of the others, hydrogen or an alkyl or acyl group as defined hereinbefore, the hydroxy functions of which may be alkylated or acylated according to conventional methods, the totality of the compounds of formulae (VI$_a$), (VI$_{a1}$) and (VI$_{a2}$) and their alkylation and acylation products forming the totality of the compounds of formulae (VI), (VI$_1$) and (VI$_2$) respectively:

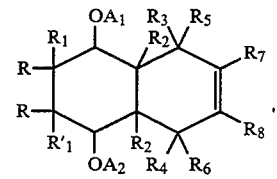
(VI)

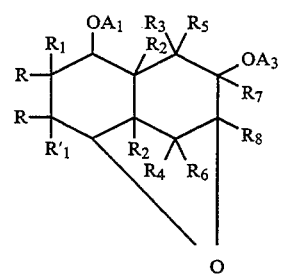
(VI$_1$)

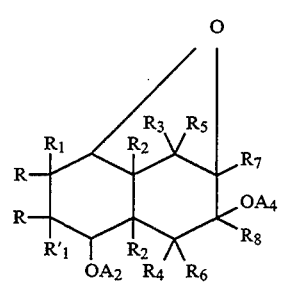
(VI$_2$)

wherein R, R$_1$, R'$_1$, R$_2$, R$_3$, R$_4$, R$_5$, R$_6$, R$_7$, R$_8$, A$_1$, A$_2$, A$_3$ and A$_4$ are as defined above, it being possible for the compounds of formula (VI) to be:

either hydrogenated, for example under atmospheric pressure, in the presence of a catalyst, such as palladium-on-carbon or platinum-on-carbon, to compounds of formula (VI$_b$):

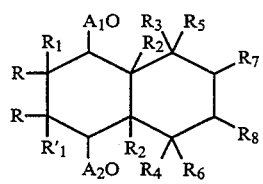
(VI$_b$)

wherein R, R$_1$, R'$_1$, R$_2$, R$_3$, R$_4$, R$_5$, R$_6$, R$_7$, R$_8$, A$_1$ and A$_2$ are as defined above, or hydroxylated, for example by the action of osmium tetroxide or potassium permanganate in the case of cis-hydroxylation, or by the action of vanadium pentoxide in the case of trans-hydroxylation, to compounds of formula (VI$_{c1}$):

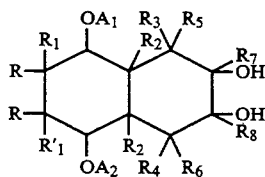

wherein R, R₁, R'₁, R₂, R₃, R₄, R₅, R₆, R₇, R₈, A₁ and A₂ are as defined above, the hydroxy functions of which may be alkylated or acylated according to conventional methods, the compounds of formula (VI$_{c1}$) and their acylation and alkylation products forming the totality of the compounds of formula (VI$_c$):

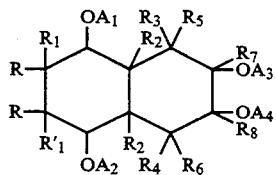

wherein R, R₁, R'₁, R₂, R₃, R₄, R₅, R₆, R₇, R₈, A₁, A₂, A₃ and A₄ are as defined above,
or treated with an oxidising agent, such as 3-chloroperbenzoic acid, to obtain the compound of formula (VI$_d$):

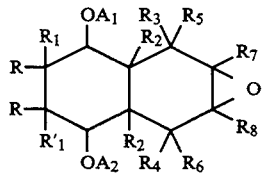

wherein R, R₁, R'₁, R₂, R₃, R₄, R₅, R₆, R₇, R₈, A₁ and A₂ are as defined above,
the totality of the compounds of formulae (VI), (VI₁), (VI₂), (VI$_b$), (VI$_c$) and (VI$_d$) forming the totality of the compounds of formula (I) which, if desired, are purified in accordance with a conventional method of purification, and separated into their possible stereoisomers in accordance with conventional methods of separation, and converted into their possible pharmaceutically-acceptable addition salts with a base.

The applicant has discovered that the compounds of the invention are very useful for any pathology presenting an anomaly in the secretion of insulin, whether a deficit, such as in diabetes or insulin resistance, or a hypersecretion of insulin, a risk factor encountered in cardiovascular disorders and also present in the case of insulinomas.

The present invention relates also to pharmaceutical compositions comprising at least one compound of formula (I), or a pharmaceutically acceptable addition salt thereof with a base, alone or in combination with one or more inert, non-toxic excipients. Among the pharmaceutical compositions according to the invention there may be mentioned more especially those suitable for oral, parenteral, nasal, rectal, perlingual, ocular or pulmonary administration, and especially injectable preparations, aerosols, eye or nose drops, tablets, film-coated tablets, dragées, soft gelatin capsules, hard gelatin capsules, suppositories, creams, ointments, dermal gels ...

The effective dosage varies in accordance with the age and weight of the patient, the administration route, the nature of the disorder and of possible associated treatments, and ranges from 0.5 mg to 1 g per 24 hours.

The following Examples illustrate the invention without, however, limiting it in any way.

The starting materials are readily available or prepared by known methods of operation.

Adopted numerotation for nomenclature of naphthalene compounds in the following examples is according to IUPAC rules, i.e. to the formula:

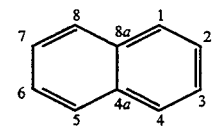

EXAMPLE 1

1,4,4aβ,5,6,7,8,8aβ-octahydro-5α,6β,7β,8α-tetraacetoxy-1β,4β-ethanonaphthalene

Step α: 1,4,4aβ,5,8,8aβ-hexahydro-5,8-dioxo-1β,4β-ethanonaphthalene 22 ml (230.9 mmols) of 1,3-cyclohexadiene are added dropwise to a solution of 25 g (230.9 mmols) of parabenzoquinone in 200 ml of toluene at room temperature and under an inert atmosphere. The reaction mixture is then stirred at 40° C. for 16 hours. The reaction is monitored by thin-layer chromatography. When the reaction is complete, the reaction mixture is concentrated under reduced pressure. The residue, triturated in petroleum ether, crystallises to yield 39.4 g of a green powder. Melting point: 93°–95° C. Yield: 91%.

Step β: 1,4,4aβ,5,8,8aβ-hexahydro-5α,8α-dihydroxy-1β,4β-ethanonaphthalene 10 g (53.1 mmols) of the compound obtained in Step α are dissolved in 2 liters of a mixture of equal volumes of dichloromethane and methanol. 19.88 g (53.4 mmols) of cerium(III) chloride heptahydrate are added in one lot at room temperature. The whole is then stirred until dissolution is complete. 2 g (53.1 mmols) of sodium borohydride are then added, in small portions, at room temperature.

When the reaction, monitored by thin-layer chromatography, is complete, the reaction mixture is concentrated under reduced pressure. The yellowish oil obtained is then taken up in ether and 7.2 g of the expected compound crystallise in the form of a white powder. Melting point: 130°–132° C. Yield: 70%.

Step γ: 1,4,4aβ,5,6,7,8,8aβ-octahydro-5α,6β,7β,8α-tetraacetoxy-1β,4β-ethanonaphthalene 11 g (57.2 mmols) of the compound obtained in Step β are dissolved in 770 ml of a tert-butanol/water/pyridine mixture (25:7:1). 35.5 ml of a 2.5% by weight solution of osmium tetroxide in tert-butanol (2.87 mmols) and then 9.6 g (86.1 mmols) of trimethylamine N-oxide are added. The whole is heated to 60° C. and maintained under magnetic stirring for 20 hours. When the reaction is complete, the excess oxidising agent is destroyed by the addition of 40 ml of a 20% aqueous solution of sodium hydrogen sulphonate. The reaction mixture is then concentrated under reduced pressure. The brown oil obtained is then dissolved in 100 ml of pyridine. 100 ml of acetic anhydride are then added dropwise and the whole is stirred for 12 hours. The reaction mixture is concentrated under reduced pressure and then chromatographed on a silica gel columto (eluant: hexane/ethyl acetate, 2:1). 14 g of the expected compound together with its trans isomer in a ratio of 90:10 are obtained. Total yield: 62%.

EXAMPLE 2

1,2,3,4,4aβ,5,6,7,8,8aβ-decahydro-2β,3β-dihydroxy-5α,6β,7β,8α-tetraacetoxy-1β,4β-ethanonaphthalene 10 g (25.4 mmols) of the compound obtained in Example 1 are dissolved in 335 ml of a tert-butanol/water/pyridine mixture (25:7:1). 16.3 ml (1.3 mmols) of a 2.5% by weight solution of osmium tetroxide in tert-butanol are then added, followed by 4.23 g (38.1 mmols) of trimethylamine N-oxide. The reaction mixture is heated to 60° C. and maintained under magnetic stirring until maximum oxidation is achieved. The excess oxidising agent is destroyed by the addition of 20 ml of a 20% aqueous sodium hydrogen sulphate solution. The whole is then concentrated under reduced pressure. The brown oil obtained is taken up in dichloromethane and washed with a saturated sodium chloride solution. Customary treatment of the organic phases yields, after purification on a silica gel column (eluant: hexane/ethyl acetate, 1:4), 5.5 g of the expected product in the form of a white powder. Melting point: 98°–100° C. Yield: 83%.

EXAMPLE 3

1,2,3,4,4aβ,5,6,7,8,8aβ-decahydro-2β,3β,5α,6β,7β,8α-hexahydroxy-1β,4β-ethanonaphthalene 2 g (4.7 mmols) of the compound obtained in Example 2 are dissolved in 100 ml of methanol and subjected to deacetylation in the presence of Amberlite resin (OH⁻). The reaction is monitored by thin-layer chromatography. After filtration, the solution is concentrated under reduced pressure to yield 828 mg of a white powder corresponding to the expected product. Melting point: 188°–192° C. Yield: 69%.

EXAMPLE 4

1,4,4aβ,5,6,7,8,8aβ-octahydro-5α,6β,7β,8α-tetrahydroxy-1β,4β-ethanonaphthalene

This compound is obtained in a manner identical to that described in Example 1, the synthesis being stopped in Step γ before acetylation of the compound. Melting point: 172° C. (decomposition).

EXAMPLE 5

1,2,3,4,4aβ,5,6,7,8,8aβ-decahydro-3α,5α-epoxymethano-2β,6β,7β,8α-tetraacetoxy-1β,4β-ethanonaphthalene Step α: 1,4,4aβ,5,6,7,8,8aβ-octahydro-3α,5α-epoxymethano-2β,8αdihydroxy-1β,4β-ethanonaphethalene 13.4 g (69.7 mmols) of the compound obtained in Example 1, Step β, are dissolved in 1 liter of dichloromethane. There are added in small portions to that solution, cooled with an icebath, 18.9 g (76.7 mmols) of 3-chloroperbenzoic acid. The whole is stirred at 0° C. for 1 hour, then at room temperature until the starting material has disappeared completely (reaction monitored by thin-layer chromatography). The whole is then cooled to −78° C. and the resulting precipitate is quickly filtered off. The filtrate, concentrated under reduced pressure, yields a yellowish oil which is chromatographed on a silica gel columto (eluant: hexane/ethyl acetate, 1:4). 10.3 g of the expected compound are thus obtained in the form of a white powder. Melting point: 140°–143° C. Yield: 71%.

Step β: 1,2,3,4,4aβ,5,6,7,8,8aβ-decahydro-3α,5α-epoxymethano-2β,6β,7β,8α-tetraacetoxy-1β,4β-ethanonaphthalene 6 g (28 mmols) of the compound obtained in the preceding Step are subjected to the action of 2.93 ml (0.29 mmols) of a 2.5% by weight solution of osmium tetroxide in tert-butanol, in the presence of 5 g (43.2 mmols) of N-methylmorpholine N-oxide, in 80 ml of a tetrahydrofuran/tert-butanol/water mixture (20:13:6). The crude product of the reaction is acetylated in accordance with the method described in Example 1, Step γ.

The reaction mixture is concentrated under reduced pressure and then chromatographed on a silica gel column (eluant: hexane/ethyl acetate, 4:1 ) to yield the expected product. Melting point: 154°–157° C.

EXAMPLE 6

1,2,3,4,4aβ,5,6,7,8,8aβ-decahydro-3α,5α-epoxymethano-2β,6β,7β,8α-tetrahydroxy-1β,4β-ethanonaphthalene The process is identical to that described for Example 3, starting from the compound obtained in Example 5. Melting point: 208°–210° C.

The compounds of Examples 7 to 11 were obtained by proceeding as described in Example 1, replacing the cyclohexadiene with the appropriate diene.

EXAMPLE 7

1,4,4aβ,5,6,7,8,8aβ-octahydro-5α,6β,7β,8α-tetraacetoxy-1β,4β-methanonaphthalene

EXAMPLE 8

1,4,4aβ,5,6,7,8,8aβ-octahydro-1α,4α,5α,6β,7β,8α-hexaacetoxynaphthalene

EXAMPLE 9

1,4,4aβ,5,6,7,8,8aβ-octahydro-5α,6β,7β,8α-tetraacetoxy-2,3-dimethylnaphthalene

EXAMPLE 10

1,4,4aβ,5,6,7,8,8aβ-octahydro-5α,6β,7β,8α-tetraacetoxy-1α-methyl-4α-isopropylnaphthalene

EXAMPLE 11

1,4,4aβ,5,6,7,8,8aβ-octahydro-5α,6β,7β,8α-tetraacetoxy-1α-methyl-4α-propyl-1β,4β-ethanonaphthalene The compounds of Examples 12 to 16 are obtained starting from the compounds of Examples 7 to 11, respectively, by proceeding in accordance with the method of operation described in Example 4.

EXAMPLE 12

1,4,4aβ,5,6,7,8,8aβ-octahydro-5α,6β,7β,8α-tetrahydroxy-1β,4β-methanonaphthalene

EXAMPLE 13

1,4,4aβ,5,6,7,8,8aβ-octahydro-1α,4α,5α,6β,7β,8α-hexahydroxynaphthalene Melting point: 59°–62° C.

EXAMPLE 14

1,4,4aβ,5,6,7,8,8aβ-octahydro-5α,6β,7β,8α-tetrahydroxy-2,3-dimethylnaphthalene

EXAMPLE 15

1,4,4aβ,5,6,7,8,8aβ-octahydro-5α,6β,7β,8α-tetrahydroxy-1α-methyl-4α-isopropylnaphthalene

EXAMPLE 16

1,4,4aβ,5,6,7,8,8aβ-octahydro-5α,6β,7β,8α-tetrahydroxy-1α-methyl-4α-isopropyl-1β,4β-ethanonaphthalene Melting point: 183°–184° C.

Examples 17 to 22 are obtained in accordance with the method of operation described in Example 3, starting from para-benzoquinone and the appropriate diene.

EXAMPLE 17

1,2,3,4,4aβ,5,6,7,8,8aβ-decahydro-2β,3β,5α,6β,7β,8α-hexahydroxy-1β,4β-methanonaphthalene Melting point: 162°–164° C.

EXAMPLE 18

1,2,3,4,4aβ,5,6,7,8,8aβ-decahydro-1α,2β,3β,4α,-5α,6β,7β,8α-octahydroxynaphthalene Melting point: 262° C. (decomposition)

EXAMPLE 19

1,2,3,4,4aβ,5,6,7,8,8aβ-decahydro-2β,3β,5α,6β,7β,8α-hexahydroxy-2α,3α-dimethylnaphthalene Melting point: 212°–214° C.

EXAMPLE 20

1,2,3,4,4aβ,5,6,7,8,8aβ-decahydro-2β,3α,5α,6β,7β,8α-hexahydroxy-2α,3β-dimethylnaphthalene Melting point: 215°–217° C.

EXAMPLE 21

1,2,3,4,4aβ,5,6,7,8,8aβ-decahydro-2β,3β,5α,6β,7β,8α-hexahydroxy-1α-methyl-4α-isopropylnaphthalene

EXAMPLE 22

1,2,3,4,4aβ,5,6,7,8,8aβ-decahydro-2β,3β,5α,6β,7β,8α-hexahydroxy-1α-methyl-4α-isopropyl-1β,4β-ethanonaphthalene Melting point: (lyophilised product)

$^1$H NMR (DMSO), δ(ppm): 5.60 (2H, m); 4.8 (1H, d); 4.75 (1H, d); 4.48 (1H, d) 4.30 (2H, m); 4.1 (1H, t); 3.85 (2H, m); 3.75 (1H, m); 3.68 (1H, m); 2.05 (1H, dd); 1.9 (1H, dd) 1.8 to 1.5 (3H, m); 1.15 (1H, m); 0.9 (3H,,d); 0.85 (3H, s); 0.82 (1H, m).

EXAMPLE 23

1,2,3,4,4aβ,5,6,7,8,8aβ-decahydro-5α,6β,7β,8α-tetraacetoxy-1β,4β-ethanonaphthalene 800 mg of the compound obtained in Example 1 are dissolved in 30 ml of a methanol/ethyl acetate mixture (1:1). 80 mg of palladium-on-carbon are then added. The mixture is stirred in the presence of hydrogen at atmospheric pressure until the starting material has disappeared completely. After filtration over Celite, the filtrate is concentrated under reduced pressure. 700 mg of the expected compound are obtained. Yield: 90%.

$^1$H NMR (DMSO), δ(ppm): 5.35 (2H, m); 5.24 (2H, m); 2.45 (2H, m); 2.00 (12H, s); 1.7 to 1.45 (10H, m).

By proceeding in the same manner starting from the compounds obtained in Examples 8 and 11, Examples 24 and 25, respectively, are obtained.

EXAMPLE 24

1,2,3,4,4aβ,5,6,7,8,8aβ-decahydro-1α,4α,5α,6β,7β,8α-hexa-acetoxynaphthalene

EXAMPLE 25

1,2,3,4,4aβ,5,6,7,8,8aβ-decahydro-5α,6β,7β,8α-tetraacetoxy-1α-methyl-4α-isopropyl-1β,4β-ethanonaphthalene The following three Examples are obtained by deacetylation of the compounds obtained in Examples 23, 24 and 25, respectively, in accordance with the method of operation described in Example 4.

EXAMPLE 26

1,2,3,4,4aβ,5,6,7,8,8aβ-decahydro-5α,6β,7β,8α-tetrahydroxy-1β,4β-ethanonaphthalene Melting point: 182°–185° C. (decomposition).

EXAMPLE 27

1,2,3,4,4aβ,5,6,7,8,8aβ-decahydro-1α,4α,5α,6β,7β,8α-hexahydeoxymaphthalene

Melting point: (mousse) (55° C.).

EXAMPLE 28

1,2,3,4,4aβ,5,6,7,8,8aβ-decahydro-5α,6β,7β,8α-tetrahydroxy-1α-methyl -4α-isopropyl-1β,4β-ethanonaphthalene

EXAMPLE 29

1,2,3,4,4aβ,5,6,7,8,8aβ-decahydro-2β,3β-epoxy-5α,6β,7β,8α-tetraacetoxy-1β,4β-ethanonaphthalene 1 g (2.6 mmols) of the compound obtained in Example 1 are dissolved in 40 ml of dichloromethane. There are added in small portions to that solution, cooled with an ice bath, 1.42 g (5.76 mmols) of 70% 3-chloroperbenzoic acid. The solution is stirred at 0° C. for 1 hour, then at room temperature until the starting material has disappeared completely (reaction monitored by thin-layer chromatography). The reaction mixture is then cooled to −78° C., and the resulting precipitate is quickly filtered off. The filtrate is then concentrated under reduced pressure, and the yellowish oil so-obtained is chromatographed on a silica gel column (eluant: dichloromethane/ethyl acetate 10:1). 140 mg of the expected compound are obtained in the form of a white powder. Yield: 90% Melting point: 186°–188° C.

EXAMPLE 30

1,2,3,4,4aβ,5,6,7,8,8aβ-decahydro-2β,3β-dihydroxy-5α,6β,7β,8α-tetraacetoxy-2α,3α-dimethylnaphthalene The compound obtained in Example 9 is subjected to the hydroxylation reaction described in Example 2. Melting point: 169°–171° C.

By proceeding as described for the preparation of Example 6, each time isolating the isomer concerned, the following compounds are obtained.

EXAMPLE 31

1,2,3,4,4a$\beta$,5,6,7,8,8a$\beta$-decahydro-2$\beta$,6$\beta$,7$\alpha$,8$\alpha$-tetrahydroxy-3$\alpha$,5$\alpha$-epoxymethano-1$\beta$,4$\beta$-ethanonaphthalene Melting point: 208°–211° C.

EXAMPLE 32

1,2,3,4,4a$\beta$,5,6,7,8,8a$\beta$-decahydro-2$\beta$,6$\beta$,7$\beta$,8$\alpha$-tetrahydroxy-3$\alpha$,5$\alpha$-epoxymethano-1$\alpha$-methyl-4$\alpha$-isopropyl-1$\beta$,4$\beta$-ethanonaphthalene Melting point: (lyophilisate) $^1$H NMR (DMSO), $\delta$(ppm): 4.78 (1H, d); 4.5 (1H, d); 4.3 (1H, d); 4.15 (1H, d) 3.88 (1H, m); 3.8 (2H, m); 3.48 (2H, m); 3.3 (1H, m); 2.26 (1H, m); 2.05 (1H, m); 1.68 (1H, m); 1.65 to 1.45 (3H, m); 1.03 (3H, s); 0.85 (3H, d); 0.82 (1H, m).

EXAMPLE 33

1,2,3,4,4a$\beta$,5,6,7,8,8a$\beta$-decahydro-2$\beta$,6$\beta$,7$\beta$,8$\beta$-tetrahydroxy-3$\alpha$,5$\alpha$-epoxymethano-1$\alpha$-isopropyl-4$\alpha$-methyl-1$\beta$,4$\beta$-ethanonaphthalene Melting point: (lyophilisate)
$^1$H NMR (DMSO), $\delta$(ppm): 5.25 (1H, d); 5.05 (1H, d); 4.75 (1H, d); 4.65 (1H, d); 4.05 (1H, m); 4.0 (1H, m), 3.7 (1H, m); 3.45 (2H, m); 3.22 (1H, m); 2.15 (1H, m); 2.0 (1H, m); 1.7 (1H, m); 1.6 to 1.5 (4H, m); 0.98 (3H, d); 0.95 (3H, s); 0.88 (3H, d).

EXAMPLE 34

1,2,3,4,4a$\beta$,5,6,7,8,8a$\beta$-decahydro-2$\beta$,6$\beta$,7$\alpha$,8$\beta$-tetrahydroxy-3$\alpha$,5$\alpha$-epoxymethano-1$\alpha$-isopropyl-4$\alpha$-methyl-1$\beta$,4$\beta$-ethanonaphthalene Melting point: (lyophilisate)
$^1$H NMR (DMSO), $\delta$(ppm): 4.9 (1H, d); 4.8 (1H, d); 4.5 (1H, d); 4.05 (1H, d); 3.8 (1H, d); 3.42 (1H, m); 3.35 (2H, m); 3.15 (1H, m); 3.08 (1H, m); 1.95 (1H, m); 1.55 (2H, m); 1.0 (2H, m); 0.95 to 0.85 (9H, m).

PHARMACOLOGICAL STUDY

EXAMPLE A

Measurement of the secretion of insulin in vitro

This test is carried out by static incubation of isolated islets of Langerhans. In practice, the islets of Langerhans are isolated from exocrinal pancreatic tissue by digestion with collagenase. After selection, the islets are incubated in a glucose-containing medium at 37° C. The quantity of insulin released is measured by radio-immunological determination.

1-Isolation of the islets

The animals are non-fasting Sprague Dawley rats (Ch. River) weighing from 250–350 g that have been anaesthetized with sodium pentobarbital (Nembutal, 40 mg/kg i.p.).

A median laparotomy is carried out in order to obstruct the bile duct by ligature at the level of the duodenum. A catheter is introduced into the duct at the hepatic level. The pancreas is distended by 20 ml of Hank's medium at 4° C. using a syringe connected to the catheter. The pancreatic tissue is quickly removed, rinsed and adhering fat is removed. It is then transferred to a beaker containing Hank's medium at 4° C. and cut up finely with scissors for 5 to 6 minutes. After sedimentation, the tissue fragments are placed in a sterile 10 ml tube of silicone glass containing 2 ml of Hank's medium in which collagenase has been dissolved. The whole is vortex-mixed for 3 minutes under a lamp fitted with a 100 W bulb. When a temperature of 37° C. is reached, a more violent agitation (rapid back and forth movements) is maintained for a further 2 or 3 minutes. The digestion is stopped by filling the tube with Hank's medium at 4° C. and by centrifugation for 1 minute at 2500 g. The supernatant is removed. That operation is repeated twice. The final residue is taken up in 10 ml of Hank's medium and observed with a binocular magnifying glass.

The most dense islets of Langerhans (100–150 by digestion), with sharp contours and of ovoid shape, are removed using a Pasteur pipette. Islets still surrounded by exocrinal pancreatic tissue indicate too gentle a digestion. Islets having a translucent appearance, with slashed contours, are a sign of too aggressive a digestion.

2-Static incubation of the islets

After selection, the islets are transferred to a Petri dish containing Krebs Bicarbonate buffer (KRB), pH 7.4, augmented with glucose to 2.8 mM. The islets are then divided into sets of 10 in haemolysis tubes (13×75 mm) that have previously been filled with 2 ml of the same buffer. That period of pre-incubation is carried out in a water bath at 37° C. for one hour with a continuous flow of carbogen. The insulin released during that period is removed by washing in the KRB buffer augmented with glucose to 2.8 mM.

The islets are incubated for 60 minutes in 2.5 ml of KRB buffer, it being possible for the concentration of glucose, depending on the protocol followed, to be 2.8 mM (basal secretion), 7 or 11 mM (sub-maximum secretion) or 16.7 mM (maximum secretion).

After gentle vortex-mixing of the tubes and centrifugation for 1 minute at 2500 g, 2 aliquot fractions of 50 ml are removed from each tube and stored in a freezer at $-20°$ C.

3-Determination of the quantity of insulin secreted

The quantity of insulin secreted during incubation of the islets of Langerhans is evaluated by radio-immunological determination carried out with the Phadeseph RIA Insulin Kit (PHARMACIA). The islets are incubated with two concentrations of glucose, one basal (2.8 mM) and the other simulating the secretion of insulin (16.7 mM). The results are expressed as a percentage of the effect of the glucose. All the products were tested at a concentration of 0.1 mM.

TABLE I

Effects of the compounds on the secretion of insulin from the isolated islets of Langerhans of normal Sprague Dawley rats

| COMPOUNDS | GLUCOSE | |
|---|---|---|
| | 2,8 mM | 16,7 mM |
| Ex. 2 | −60,5 | −22,6 |
| Ex. 3 | −18,3 | 43,9 |
| Ex. 6 | −5,7 | −70,4 |
| Ex. 13 | −33,3 | −24,8 |
| Ex. 19 | −16,1 | 0,8 |
| Ex. 20 | −59,7 | 1,5 |
| Ex. 22 | −30,8 | −29,0 |
| Ex. 26 | −15,7 | 18,3 |
| Ex. 30 | −44,6 | −0,9 |
| Ex. 31 | −33 | −14,5 |
| Ex. 33 | 19,4 | 17,3 |

TABLE I-continued

Effects of the compounds on the secretion of insulin from the isolated islets of Langerhans of normal Sprague Dawley rats

| COMPOUNDS | GLUCOSE | |
|---|---|---|
| | 2,8 mM | 16,7 mM |
| Ex. 34 | −4,1 | 14,4 |

We claim:

1. A compound selected from those of formula (I):

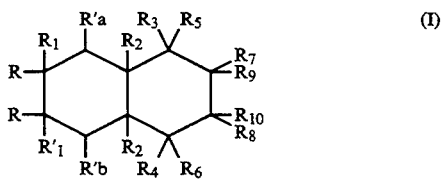

wherein:

R represents a radical selected from hydroxy, alkoxy and acyloxy, $R_1$, $R'_1$ and $R_2$ are each selected, independently of the others, from hydrogen and alkyl, the two $R_2$ groups being in the cis position in relation to the rings, $R_3$ and $R_4$ each represents hydrogen or together form a methylene or ethylene bridge, $R_5$ and $R_6$ are each selected, independently of the other, from hydrogen, hydroxy, alkoxy, acyloxy and alkyl, $R_7$ and $R_8$ are each selected, independently of the other, from hydrogen and alkyl, $R_9$, $R_{10}$, R'a and R'b
are each selected, independently of the others, from hydrogen, hydroxy, alkoxy and acyloxy, or $R_9$ and $R_{10}$ together form a double bond or a ring with an oxygen atom and R'a and R'b are as defined above, or $R_9$ and R'a together form a ring with an oxygen atom and $R_{10}$ and R'b are as defined above, or $R_{10}$ and R'b together form a ring with an oxygen atom and $R_9$ and R'a are as defined above, it being understood that the terms "alkyl", "alkoxy"0 and "acyloxy" denote straight-chain or branched groups having 1 to 6 carbon atoms inclusive, its stereoisomers, and also its possible pharmaceutically-acceptable addition salts with a base.

2. A compound according to claim 1, selected from those wherein $R_2$ represents hydrogen, its stereoisomers, and also its possible pharmaceutically-acceptable addition salts with a base.

3. A compound according to claim 1, selected from those wherein $R_1$ represents hydrogen, its stereoisomers, and also its possible pharmaceutically-acceptable addition salts with a base.

4. A compound according claim 1, which is selected from 1,2,3,4,4a$\beta$,5,6,7,8,8a$\beta$-decahydro-2,3,5,6,7,8-hexahydroxy-1,4-ethanonaphthalene, its stereoisomers, and its possible pharmaceutically-acceptable addition salts with a base.

5. A compound according to claim 1, which is selected from 1,4,4a$\beta$,5,6,7,8,8a$\beta$-octahydro-5,6,7,8-tetrahydroxy-1,4-ethanonaphthalene, its stereoisomers, and its possible pharmaceutically-acceptable addition salts with a base.

6. A compound according to claim 1, which is selected from 1,4,4a$\beta$,5,6,7,8,8a$\beta$-octahydro-1,4,5,6,7,8-hexahydroxynaphthalene, its stereoisomers, and its possible pharmaceutically-acceptable addition salts with a base.

7. A compound according to claim 1, which is selected from 1,2,3,4,4a$\beta$,5,6,7,8,8a$\beta$-decahydro-2,3-epoxy-5,6,7,8-tetraacetoxy-1,4-ethaninaphthalene, its stereoisomers, and its possible pharmaceutically-acceptable addition salts with a base.

8. A compound according to claim 1, which is selected from 1,2,3,4,4a$\beta$,5,6,7,8,8a$\beta$-decahydro-2,6,7,8-tetrahydroxy-3,5-epoxymethano-1-methyl-4-isopropyl-1,4-ethanonaphthalene, its stereoisomers, and its possible pharmaceutically-acceptable addition salts with a base.

9. A compound according to claim 1, which is selected from 1,2,3,4,4a$\beta$,5,6,7,8,8a$\beta$-decahydro-2$\beta$,3$\beta$,5$\alpha$,6$\beta$,7$\beta$,8$\alpha$-hexahydroxy-1$\beta$,4$\beta$-ethanonaphthalene and its possible pharmaceutically-acceptable addition salts with a base.

10. A method for treating a mammal afflicted with a disease requiring a compound which regulates the secretion of insulin, comprising the step of administering to said mammal an amount of a compound of claim 1 which is effective for alleviation of said disease.

11. A pharmaceutical composition useful in regulating insulin resistance comprising an effective amount of a compound as claimed in claim 1, in combination with a pharmaceutically-acceptable excipient or vehicle.

* * * * *

UNITED STATES PATENT AND TRADEMARK OFFICE
CERTIFICATE OF CORRECTION

PATENT NO. : 5,422,365
DATED : June 6, 1995
INVENTOR(S) : David Billington, Francoise Perron-Sierra, Isabelle Picard, Jacques Duhault, Joseph Espinal It is certified that error appears in the above-indentified patent and that said Letters Patent is hereby corrected as shown below:

Column 2, line 60; 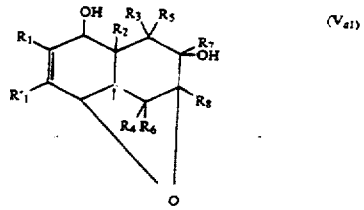

should read 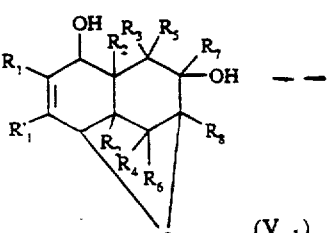 one ($R_2$ was missing).

Column 3, line 22; "cis" should read -- *cis* --
Column 3, line 28; "trans" should read -- *trans* --
Column 4, line 66; "cis" should read -- *cis* --
Column 4, line 67; "trans" should read -- *trans* --
Column 7, line 1; "colunto" should read -- column --
Column 7, line 3; "trans" should read -- *trans* --
Column 7, line 67; "colunto" should read -- column --
Column 8, line 61; "-4a-propyl-" should read
    -- -4a-isopropyl- --
Column 10, line 34; "hexahydeoxymaphthalene" should read
    -- hexahydroxynaphthalene --
Column 13, line 25; "cis" should read -- *cis* --

UNITED STATES PATENT AND TRADEMARK OFFICE
CERTIFICATE OF CORRECTION

PATENT NO. : 5,422,365

DATED : June 6, 1995    Page 2 of 2

INVENTOR(S) : David Billington, Francoise Perron-Sierra, Isabelle Picard, Jacques Duhault, Joseph Espinal It is certified that error appears in the above-indentified patent and that said Letters Patent is hereby corrected as shown below:

```
Column 13, line 45; delete the "O" at the end of the line.
Column 14, line  9; -insert the word -- to -- after "according"
     and before "claim"
Column 14, line 26; "ethaninaphthalene" should read
     -- ethanonaphthalene --
```

Signed and Sealed this

Fifth Day of September, 1995

Attest:

BRUCE LEHMAN

*Attesting Officer*    *Commissioner of Patents and Trademarks*